United States Patent [19]

Llinas et al.

[11] Patent Number: 4,897,426

[45] Date of Patent: Jan. 30, 1990

[54] METHOD FOR BLOCKING CALCIUM CHANNELS

[75] Inventors: Rodolfo R. Llinas, New York, N.Y.; Yosef Yarom, Jerusalem, Israel

[73] Assignee: New York University, New York, N.Y.

[21] Appl. No.: 341,271

[22] Filed: Apr. 20, 1989

Related U.S. Application Data

[63] Continuation of Ser. No. 213,466, Jun. 29, 1988, abandoned, which is a continuation of Ser. No. 837,088, Mar. 6, 1986, abandoned.

[51] Int. Cl.$^4$ .......................................... A61Q 31/040
[52] U.S. Cl. ..................................................... 514/724
[58] Field of Search ........................................ 514/724

[56] References Cited

U.S. PATENT DOCUMENTS

| | | | |
|---|---|---|---|
| 2,903,396 | 9/1959 | Saunders et al. | 514/724 |
| 3,041,237 | 6/1962 | Hopp et al. | 514/724 |
| 3,778,509 | 12/1973 | Lewis | 514/724 |

OTHER PUBLICATIONS

Merck Index, 9th Ed. (1976), p. 879.
Kitagawa, S., et al., *Biochem. Biophys. Acta.* 798: 210–215, 1984.
Michaelis, M. L. et al., *Biochem Pharm.* 32: 963–969, 1983.
Leslie et al., *J. Pharm. Exp. Ther.* 225: 571–575, 1983.
Requena, J., et al., *J. Gen. Physiol.* 85: 798–804, 1985.
Llinas, R. R., *In Movement Disorders: Tremor*, Findley, L. J. and Capildeo, R., eds. pp. 475–477, 1984.
Adams, R. D., *In Harrison's Principles of Internal Medicine*, Isselbacher, K. J. et al., eds. p. 96, McGraw-Hill, 1980.
Llinas, R. R., et al., *J. Physiol.* 315: 369–584, 1981.
Llinas, R. R., *In Movement Disorders: Tremor*, Findley, L. J. and Capildeo, R., eds. pp. 165–182, 1984.
Llinas, R. R. et al., *Brain Res.* 294: 127–132, 1984.
Llinas, R. R., et al., *J. Physiol.* 315: 549–567, 1981.
Jahnsen, H. et al., *J. Physiol.* 349: 227–247, 1984.
Spray, D. C. et al., *Am. J. Physiol.* 248: H753–H764, 1985.
Siggins, G. R., et al., *Ann. N.Y. Acad. Sci.* 492: 350–366, 1987.
Llinas, R., et al., *J. Physiol.* 305: 197–213, 1980.
Llinas, R., et al., *J. Physiol.* 305: 171–195, 1980.

*Primary Examiner*—Stanley J. Friedman
*Attorney, Agent, or Firm*—Darby & Darby

[57] ABSTRACT

The partial or total blocking of low threshold calcium channels in cell membranes with the use of aliphatic alcohols.

21 Claims, 6 Drawing Sheets

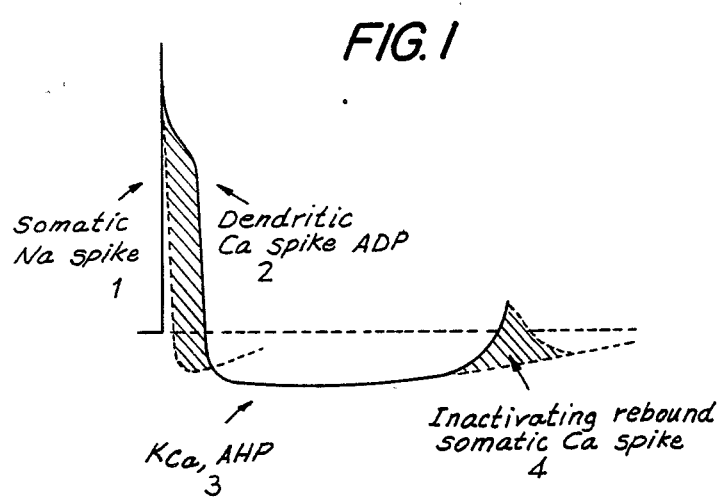
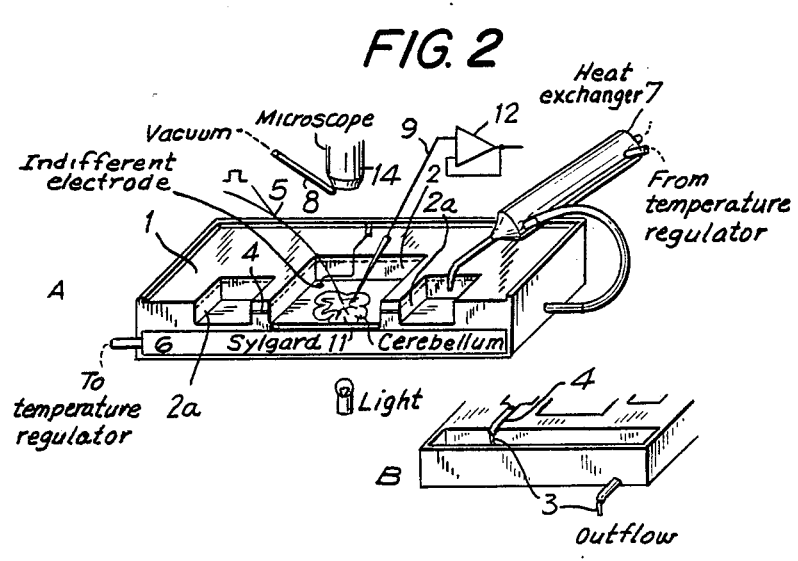

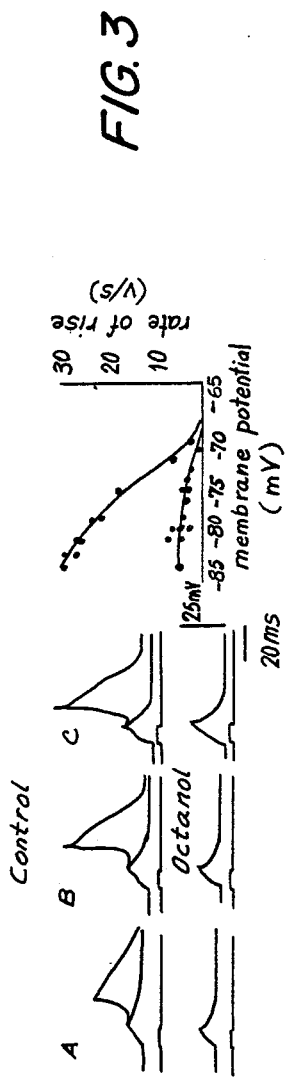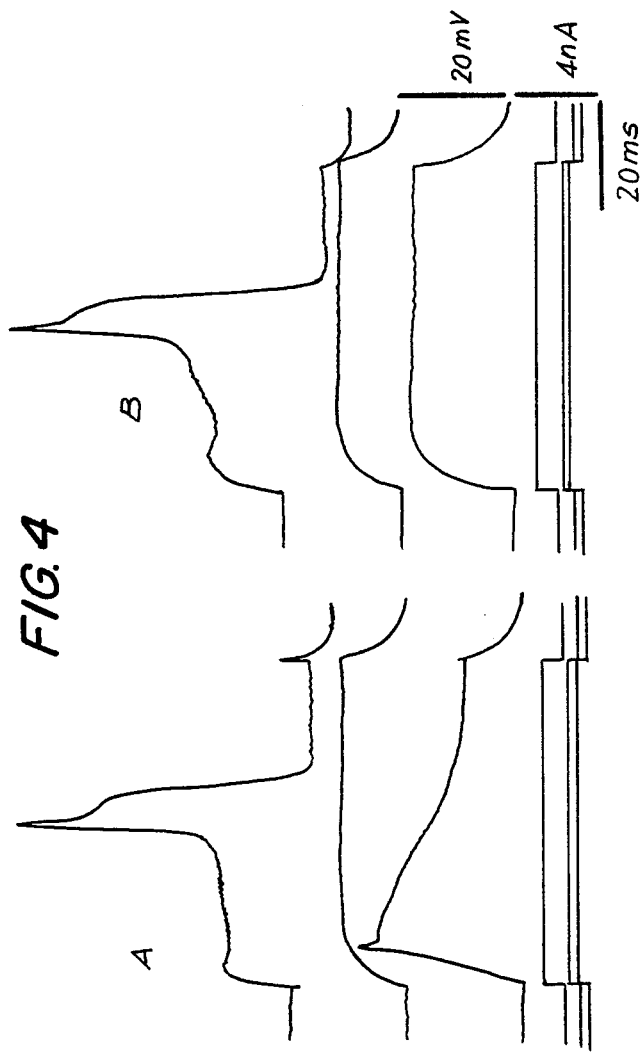
FIG. 3
FIG. 4

FIG. 8
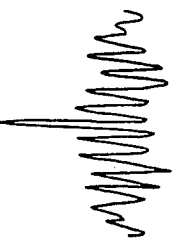
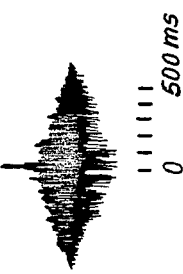
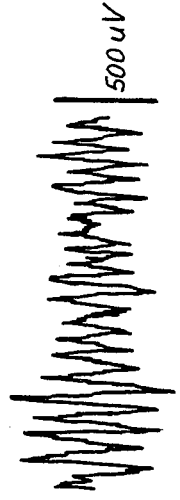
Autocorrelogram
Electromyogram
Control
Harmaline
Harmaline & 1-Octanol
500 µV
500 ms
0    500 ms

METHOD FOR BLOCKING CALCIUM CHANNELS

This is a continuation of application Ser. No. 213,466 filed June 29,1988, which in turn is a continuation of application Ser. No. 837,088 filed Mar. 6, 1986, both now abandoned.

FIELD OF THE INVENTION

This invention relates to methods and compositions for regulating calcium conductance across cell membranes. More particularly, this invention relates to methods and compositions for blocking "low-threshold" calcium channels and for treating the symptoms of tremors and other pathological conditions associated with, or controlled by, low-threshold calcium conductance.

BACKGROUND OF THE INVENTION

Neurons of the central nervous system transmit information via electrical impulses. These impulses are generated by electrochemical potentials caused by the movement of charged particles across (i.e. through) the cell membrane. The size of the impulse transmitted is a function of the membrane conductance The term "conductance," as applied to transmission of ionic charge across a cell membrane, means the incremental current (or current-like) response exhibited through the cell membrane as a result of the application of a voltage (an incremental change in the electric field) across the membrane.

A calcium channel is a structure that spans the thickness of the lipid bilayer in cell membranes and allows calcium ions to move passively across this lipid bilayer according to the calcium electrochemical gradient between the interior of the cell (where calcium concentration is lower) and the extra-cellular fluid (where calcium concentration is higher). These channels demonstrate a higher specificity for the movement of the calcium ion across this channel-like structure, although a calcium channel's selectivity with respect to other divalent cations is never perfect. Calcium channels can be activated by changes in the electric field of the cell membrane.

A calcium pump is a different structural moiety (probably one or more macromolecules) of the cell membrane. This moiety spans the cell membrane and produces an active movement of calcium ions against their electrochemical gradient. Ion pumps are therefore different from ion channels in that they require energy to generate ionic movement since ionic flow through a pump occurs against the electrochemical gradient.

In a resting state, the interior of a nerve cell is negatively charged with respect to the extracellular medium or environment. This difference in potential, which is observed across the cell membrane, is reversed when an impulse passes along the nerve. For a brief period of time, the polarity of the nerve cell becomes positive. This sequence of events is known as an "action potential."

Direct stimulation of neurons in vitro produces action potentials having two main components: a fast spike, due to sodium conductance, and a slower, calcium-dependent spike (Llinas, R. and Sugimori, M. *J. Physiol.* 305:197–213 1980). Sodium-dependent potentials are the prominant feature of the somatic (or cell-body) response, while calcium-dependent action potentials are more apparent in the dendrites.

Llinas and Yarom (*J. Physiol.* 315: 549–567; *J. Physiol.* 315: 569–584, 1981) have previously disclosed that guinea-pig inferior olivary (I.O.) cells from the brainstem exhibit a calcium-dependent conductance which also has two components. The sodium- and calcium-dependent conductance is illustrated in FIG. 1. Using techniques described below, the authors found that stimulation of these cells in vitro generates action potentials comprising a fast spike, 1 (due to sodium conductance) followed by an after-depolarization potential (ADP), 2. The ADP was shown to be due to the activation of a high-threshold calcium conductance (HTCC). The ADP was followed by an after-hyperpolarization potential (AHP), 3. In turn, the AHP was followed by a rebound depolarization spike, 4. The rebound spike (RS) was shown to be due to the activation of low-threshold calcium conductance (LTCC). The shaded areas in FIG. 1 represent the two types of voltage spikes due to the two types of calcium conductance. The ADP and AHP are tetrodo-toxin-insensitive (textrodoxin inhibits sodium conductance) and, therefore, they cannot be due to sodium conductance. The following can be considered an operative definition of the RS (or LTC spike):

The RS is generated by the presence of LTCC as follows:

(a) Following tetrodoxin poisoning of the cell membrane, the RS occurs as the membrane is abruptly depolarized with square voltage pulses of increasing amplitude, if the membrane potential is more negative than $-70$ mV. The threshold in the inferior olivary cells studied by the present invention is 65 mV.

(b) The RS occurs as a rebound action potential following hyperpolarization of the cell membrane from a resting potential. The firing level of the RS spike for the inferior olivary cells studied by the present inventors is the same as in (a), i.e. $-65$ mV.

(c) When a voltage clamp technique (described below) is used, the RS generates an ionic current that occurs at negative values of cell membrane potential, rises to a maximum, and is then inactivated—also within the negative potential range (at about $-45$ mV for the I.O. cells studied).

HTCC is involved in dendridic action potentials, in certain components of heart action, and in synaptic transmission. LTCC appears to be a somatic response.

Tremor consists of a more or less regular rhythmic oscillation of a part of the body about a fixed point. The rate of this oscillation varies from individual to individual but, in a particular patient, the rate is fairly constant in all affected parts of the body. Tremor may be caused by specific pathological diseases (e.g. Parkinson's Disease) or be due to specific lesions in the central nervous system, or it may be of unknown origin.

From a functional point of view, tremor can be seen as a modification of the basic electrophysiological properties of cells comprising the central nervous system.

It has been suggested (Llinas, R.R. in *Movement Disorders: Tremor*, pp. 165–182, Findley, L. J. and Capildeo, R., eds., MacMillan, 1984; incorporated by reference) that the interplay between the high-threshold (or dendritic) calcium conductance and the low-threshold (or somatic) conductance could result in central oscillatory properties of nerve cells which have the same cyclic rhythmic frequence such as that found in physiological and abnormal tremor as well as in Parkinson's tremor.

The present inventors have surprisingly found that certain compounds (such as aliphatic alcohols) at extremely small amounts are capable of blocking (partially or completely) the low threshold calcium conductance (which generates the so-called rebound calcium spike). Significantly, these compounds, when used in small amounts, do not affect the high-threshold calcium conductance. Furthermore, the inventors have found that although lower alkyl alcohols have a blocking effect, the higher alcohols do so at extraordinarily low concentrations.

The prior art contains several references purporting to describe the effects of alcohols on calcium conductance, and in particular the effects of ethanol. In all instances known to the present inventors, however, the alcohols were used for a different purpose (to block HTCC, i.e., as "anaesthetics") and in amounts markedly exceeding those of the present invention.

Requena et al. (J. Gen. Physiol. 85: 789–804. 1985) disclose that exposure of squid axons to octanol, at a concentration of $10^{-4}$M, correlated with an apparent increase in the observed intracellular calcium concentration in these axons. In other words, Requena et al state that octanol interferes with the ability of the calcium ions to leave the cell by crossing the cell membrane. This phenomenon is unrelated to blockage or non-blockage of calcium channels (high- or low-threshold).

As explained above, a calcium channel is a passive transport mechanism by which calcium ions move down their electrochemical gradient. In all cells, calcium concentration is low inside the cell (e.g., $10^{-7}$M) and high in the extracellular medium (e.g., $10^{-3}$M) and so a calcium channel allows calcium to go into the cell.

By contrast, outward calcium transport takes place via "a calcium pump," an entirely different mechanism which transports calcium against a concentrational gradient (from the low concentration inside to the high concentration outside). An ion pump is therefore an active membrane structure, usually an enzyme (e.g., sodium ATPase) which requires energy (ATP: adenosine triphosphate) to carry ions across the membrane. Requena et al anaesthetize the cells and, therefore, "paralyze" the pump mechanism. In any event, Requena's observations concern a totally different phenomenon from that of the present invention and require different (markedly higher) octanol concentrations. If the present inventors measured the intracellular calcium concentration after exposure of neuron cells to the alcohol in accordance with the present invention, they would observe a normal, or a lower-than-normal intracellular calcium concentration, (i.e. an effect opposite to that said to have been observed by Requena et al.), which would be due to inability of calcium to enter the cell through the blocked Ca channel. Furthermore, investigations conducted by the present inventors revealed no evidence of the presence of a low-threshold calcium channel in squid axons (unpublished observation).

Similarly, Leslie et al. (J. Pharm. Exp. Ther. 225:571–575. 1983) disclosed that ethanol, at $2.5\times10^{-2} - 1.5\times10^{-1}$M, inhibited voltage-dependent calcium uptake into synaptosomes isolated from rat brains. Aside from the high ethanol concentrations said to be used, there was no mention in this publication of studies on low-conductance calcium channels.

Michaels et al. (Biochem. Pharm. 32:963–969, 1983) described the effects of ethanol ($10^{-1}$M), propanol ($10^{-2}$M) and butanol ($10^{-1}$M) on calcium-dependent fluxes in rat brain synaptic membrane vesicles. All three alcohols inhibited calcium influxes in this experimental system.

Kitagawa et al. (Biochem. Biophys. Acta 798:210–215, 1984) disclose the use of butanol ($5\times10^{-2}$M) or hexanol ($5\times10^{-3}$) as an inhibitors of calcium mobilization in bovine platelets. The mechanism in this case is a calcium pump similar to that studied by Requena et al and the authors of the other papers described above. Moreover, the LTCC has not been demonstrated in platelets, and the mechanism by which calcium enters platelets is not known.

It has been noted in the past that one or two drinks of an alcoholic beverage can abate the symptoms of familial tremor temporarily: Harrison's Principles of Internal Medicine, p. 96 Isselbacher, K. J. et al. eds. McGraw-Hill, New York, N.Y. 1980. One or two drinks of an alcohol-containing beverage would produce blood levels approximately on the order of $10^{-2}$M in ethanol, a concentration notably higher than that necessary in the present invention. Furthermore, the intoxicating and addictive properties of ethanol are well-known.

In addition, the aforementioned empirical observations were never correlated with LTCC nor with the central nervous system. For these reasons, the above-cited phenomenon has only superficial, if any, relevance to the present invention.

Current treatment for tremors comprises administration of beta-adrenergic blockers (such as propranolol hydrochloride, and its derivatives). These drugs act via a mechanism totally different from that of the present invention, and affect muscle cells as opposed to neuron cells. Beta-adrenergic blockers cause a myriad of side-effects (e.g. bronchodilation, lightheadedness, bradycardia, hallucinations, and kidney and liver abnormalities). In addition, these drugs are not effective in all patients and are harmful to some (e.g. asthmatics). Use of the present invention should lead to minimal side-effects due to the very low concentration of alcohols administered. At the preferred alcohol concentrations, primarily only LTCC would be affected and a larger patient population could be treated using the present invention instead of beta-adrenergic blockers. Furthermore, use of alcohols in accordance with the present invention could be made in conjunction with use of beta-blockers.

OBJECTS OF THE INVENTION

The present invention has several objects including, but not limited to, the following:

to provide a method and composition for partial or complete blocking low-threshold calcium channels in mammalian cells.

to provide a method and composition for treating different types of tremor including, but not limited to, enhanced physiological tremor, essential tremor, severe essential tremor, and rubral tremor.

to provide a method and composition of treating Parkinson's tremor which can be used as an adjunct to conventional therapy.

These and other objects of the present invention will be apparent to those skilled in the art in light of the present description, accompanying claims, and appended drawings.

BRIEF DESCRIPTION OF THE DRAWINGS

FIG. 1 is a diagram serving as an illustration of the action potential obtained by electrically stimulating I.O. cells.

FIG. 2 is a perspective view in two sections of a brain slice perfusion and recording system in accordance with the present invention.

FIG. 3 is a number of oscilloscope tracings and a graph showing the effect of alcohol on the low-threshold calcium conductance and action potential.

FIG. 4 is an oscilloscope tracing obtained by stimulating I.O. cells with incremental increases in current both in the presence and absence of $10^{-4}$M butanol.

FIG. 8 is an oscilloscope tracing of electromyograms (left) and autocorrelograms (right) obtained from control or harmaline-treated rats.

SUMMARY OF THE INVENTION

Figure 5:
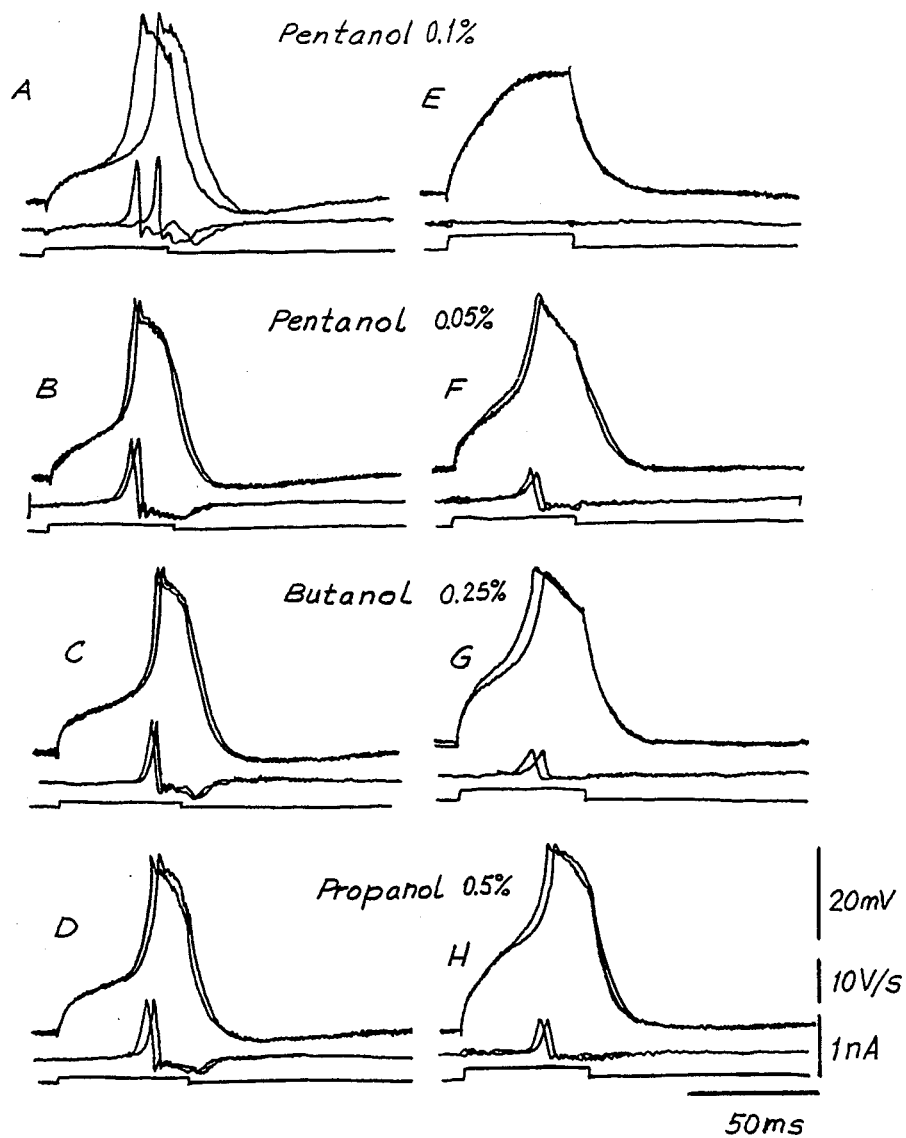
FIG. 5 is a series of oscilloscope tracings, A through H, showing the I.O. cell response to an external square current injection, in the presence of 0.1% pentanol; in the presence of 0.05% pentanol; in the presence of 0.25% butanol; in the presence of 0.5% propanol.

The present invention is directed to a method for blocking or reducing the low-threshold calcium conductance in mammalian cell membranes comprising exposing said cells to an LTCC-blocking agent (such as an aliphatic alcohol) at a concentration sufficient to block or reduce said low-threshold calcium conductance selectively. Preferably, the agent will be used at a concentration sufficiently low so that it does not affect the high-threshold calcium conductance of said cells. Preferred agents are aliphatic alcohols and particularly preferred are $C_3$–$C_{10}$ alkyl alcohols.

Another aspect of the present invention is directed to a method for inhibiting the manifestation of tremor in the muscle cells of a mammal comprising exposing central nervous system cells of said mammal to an LTCC-blocking agent (such as an aliphatic alcohol) at a concentration sufficient to impede transmission of a tremor signal from said central nervous system cells to said muscle cells. Preferably, the amount of said agent will be insufficient to interfere with the high-threshold calcium conductance in either type of cell.

Yet another aspect of the present invention relates to compositions useful in blocking LTCC or in inhibiting tremor comprising an effective amount of an LTCC-blocking or a tremor-inhibiting agent and a physiologically acceptable carrier or diluent.

DETAILED DESCRIPTION OF THE INVENTION

The present inventors have discovered that certain agents, such as aliphatic alcohols, block or reduce specifically the so-called low-threshold calcium channel in mammalian cells, and in mammalian central neurons in particular. This channel is known to be an important component in modulating the frequency of electrical discharges in central nuclei such as the inferior olive or thalamus. These agents may be used in amounts sufficient to block or reduce specifically the LTCC, without (measurably) affecting the HTCC which is involved in dendritic action potentials, in certain components of the myocardium action potential, and in synaptic transmission. Thus, the present invention provides a method for selectively blocking or reducing LTCC and thereby permits isolation of the HTCC. One use of the present invention is, therefore, in isolating and studying HTCC unencumbered by the LTCC, i.e. in a manner akin to that using tetrodotoxin to block sodium conductance.

According to the present inventors, the LTCC plays a basic role in the clocking properties of the brain, and provides a basic frequency (continuous) for the coordination of movement (which is a series of discontinuous motions). Tremor has been described as an exacerbation of the basic frequency of oscillation to the point of interference with the coordination of movement (Llinas, R. R. in *Movement Disorders: Tremor* (Findley, L. J. & Capildeo, R. Eds) pp. 16514 182 Macmillan 1984, incorporated in this application by reference).

The present inventors have further found that the same agents (e.g., aliphatic alcohols) used in the same low amounts also inhibit the symptoms of tremor.

The importance of this finding is evident from the fact that enhanced physiological tremor, essential tremor, and the tremor produced in senile patients can be completely incapacitating. The method of the present invention is advantageous in that it does not affect HTCC of either the muscle or the neuron cells. The present invention provides a method for treating the symptoms of tremor by acting on the central nervous system rather than on the muscle that exhibits the tremor response, without affecting the neuron or muscle cell functions that are associated with HTCC.

Nothing in the present disclosure or in the research that culminated in the present invention can be construed to limit applicability of the LTCC-blocking effect of the present invention to I.O. cells or even to neurons. Hence, the present invention can be used with all cells that possess low-threshold calcium channels.

According to the present invention, aliphatic alcohols are effective in blocking LTCC and in inhibiting tremor at extraordinarily low concentrations, which substantially reduces the risk of side-effects. Therefore, generally speaking, the lower the effective amount of particular alcohol, the more desirable its use.

The degree of inhibition of the low-conductance calcium channels appears to be related to the molecular weight of the alcohol (as well as the amount used). As the molecular weight increases, the effective concentration of the alcohol necessary to reduce the low-conductance potential decreases. Hence, the calcium-conductance inhibition is greater as the alcohol molecular weight is increased. This is demonstrated in detail in Example 6, below, where it is shown that pentanol, at a 5-fold lower concentration, was more effective than propanol in inhibiting LTCC (compare FIG. 5, H with E). Of course, the present inventors do not wish to be bound by any theory, based on the apparent relationship between LTCC blocking ability and alcohol molecular weight. The increasing Ca-channel-blocking ability of the higher alcohols may be due to many different factors, such as the increasing hydrophobicity of alcohols with increasing length of the hydrocarbon chain, and/or the lipid solubility of such alcohols.

The operability of the present invention has been demonstrated on living mammalian cells both in vitro and in vivo.

The absence of any abnormal behavior in the test animals employed to demonstrate the operability of the present invention provides a further strong indication that the risk of undesirable side-effects is very small.

In vitro, the cells are exposed to a culture or perfusion medium containing a LTCC-blocking effective amount of the alcohol. This amount is preferably sufficiently small so as not to interfere with HTCC. Of course, in view of the fact that different alcohols have different channel-blocking abilities, the amount will vary from alcohol to alcohol. Preferred highest molar concentrations (or preferred operative ranges for substantial and total blockage) for several of the alcohols used in the present invention are given in Table I below:

TABLE I

| Alcohol | From About | To About |
| --- | --- | --- |
| ethanol | $10^{-3}$ | $10^{-4}$ |
| propanol | $10^{-4}$ | $10^{-5}$ |
| butanol | $10^{-5}$ | $10^{-6}$ |
| pentanol | $10^{-6}$ | $10^{-7}$ |
| hexanol | $10^{-6}$ | nd[1] |
| heptanol | $10^{-6}$ | nd |
| octanol | $10^{-6}$ | nd |
| nonanol | $10^{-6}$ | nd |
| decanol | $10^{-6}$ | nd |

[1]nd - not detectable

With respect to the $10^{-6}$M figure given for hexanol through decanol above, it should be noted that the molarity could not be accurately determined. The perfusion solutions (or the parenterally administered compositions) employed in the experiments of the present inventors were made up by mixing an amount of alcohol with an amount of medium sufficient to make up a $10^{-6}$M solution, if all of the alcohol were soluble in the medium. Hence, the concentrations employed were $10^{-6}$M at most. The minimum effective concentrations could not be specified because the solubility limits of these alcohols could not be accurately determined. Nevertheless, even if all of the $C_6$-$C_{10}$ alcohol was not soluble in the medium, it continued to be effective, since control experiments employing medium that had not come in contact with alcohol did not result in either blockage of the LTCC rebound spike or in inhibition of tremor.

Moreover, the concentrations given in Table I above, are for complete blockage of LTCC. If partial blockage is desired, (as is often the case in the treatment of tremor symptoms) the amounts can be smaller, as determined by routine experimentation.

It is not to be assumed from the present discussion that the present invention is limited to use of aliphatic alcohols in solution. When alcohols are administered in vivo they can generally be administered orally, or parenterally in solid or liquid form with or without a carrier or diluent. Of course, particularly in case of oral administration, allowances should be made in the amount thus administered for any amount of alcohol that is not absorbed in the alimentary tract, or that is metabolized before reaching the blood and the cerebrospinal fluid.

Thus, the amount of the alcohol should be calculated to produce an effective LTCC-blocking (or LTCC-reducing) alcohol concentration in the vicinity of the central nervous system cells, such as that given in Table I above. To this end, the concentration of the alcohol in the composition administered to the mammal will fall in the range at which it will produce the requisite alcohol concentration in the blood, (or in the cerebrospinal fluid—CSF) as indicated in Table I, above for complete blockage. Preferably, the alcohol will be administered in a composition, also comprising a physiologically acceptable carrier or diluent. Ringer's solution or isotonic saline are preferred diluents for parenteral administration.

Most preferred, is use of octyl alcohol in an amount sufficient to generate a blood or CSF (or perfusion medium) concentration of at most $10^{-6}$M.

The above amounts will both block LTCC and also inhibit tremors.

As stated above, the amount of the LTCC-blocking or tremor-inhibiting agent will vary according to the activity of the particular agent employed and according to the mode of administration. The frequency of administration A also vary according to the extent of the tremor symptoms and according to how often they occur.

Moreover, it may be desirable in certain cases to consider employing sustained delivery systems in order to maintain an LTCC-blocking or tremor-inhibiting concentration of the active agent in the patient's bloodstream.

Nevertheless, all of the above considerations concern optimization of the use of the present invention. The dosage and mode and form of administration can be fine-tuned by routine and ordinary experimentation conducted by persons of ordinary skill in the field.

The present invention is further described below by reference to specific examples, which are intended to illustrate the present invention without limiting its scope. In these examples, LTCC rebound spike was generated by each of the three methods involved in the operational definition given in the background section of the present application. Regardless of the method (voltage clamp, square current injection or depolarization voltage) used to generate the RS, alcohols block this response, indicating that a single mechanism is at work and demonstrating the operability of the present invention.

Example 1

Tissue Preparation

Adult Hartley guinea pigs (400–600 g) from Camm Research Institute, Wayne, N.J. were decapitated, after ether anesthesia, using a small animal guillotine. Immediately thereafter, two longitudinal sections were made along the lateral edge of the squamous portion of the occipital bone. The resulting bone slab was cut transversely, and pulled caudalward to expose the cerebellum and brain stem. Following transection of the cranial nerves and transverse section of the brain stem (at the inferior collicular level rostrally and at the level of C1 caudally) the brain stem was swiftly removed and placed in aerated Ringer's solution (containing 124 mM NaCl; 5 mM KCl, 1.2 mM $KH_2PO_4$; 2.4 mM $CaCl_2$; 1.3 mM $MgSO_4$; 2.6 mM $NaHCO_3$ and 10 mM glucose) at about 5° C. It was then transected longitudinally in a parasagittal plane and fixed to a Vibratome Model G plate (available from Ted Pella, Inc., Tustin, Calif.) in order to obtain thin longitudinal sections. From a single brain stem, six 300-micron slices could be obtained. Following sectioning, the slices were incubated in Ringer's solution for approximately one hour. The bathing medium was kept at room temperature and a mixture of 95% $O_2$ and 5% $CO_2$ was bubbled into the bath during this period. Brain stem slices were removed from the incubation bath after one hour but could be kept in good condition in the bath for periods of time up to 24 hours.

EXAMPLE 2

Recording Chamber

Reference will be made to FIGS. 2A and 2B, which are perspective views in section along line A—A of the perfusion and recording system used in the present experiments.

After incubation, a slice was transferred to recording dish 1 where the tissue was continuously perfused with Ringer's solution at 37° C. The perfusion system was gravity-fed, allowing a routine flow of 0.5 ml/min. with a maximum of 2 ml/min. The latter flow rate was used during solution exchange. The central chamber 2 had a capacity of 2 ml and the solution could be completely exchanged in approximately ten minutes. The saline flowed into the central chamber through three small diameter channels 4 (one of which is shown in FIG. 2A) which produced a close-to-laminar flow. Side-chambers 2a, which communicated with chamber 2 via channels 4, were used as reservoirs for the perfusion saline. The outflow from the central chamber 2 was accomplished via a cotton wick system 3 which prevented turbulence by allowing continuous fluid movement (FIG. 2B).

The brain slice was placed on a Sylgard plate 11 Corning Glass, Corning, N.Y.) at the bottom of the recording chamber 2 and secured with a bipolar stimulating electrode 5 pressing lightly on the brain tissue. The chamber was maintained at 37° C. by a surrounding water bath 6, which kept it at the same temperature as the perfusing solution (37° C.). The saline solution itself was temperature-regulated by passage through a heat exchanger 7 at 37° C. (FIG. 2A).

The standard perfusion fluid was Ringer's solution; this medium was used during cutting and incubating, and during most of the recording time. Ringer's solution provided excellent pH-buffering properties at different temperatures. This was especially significant during the sectioning and incubation periods.

When desired, alcohols were added to the perfusion fluid by direct application into chamber 1 via the perfusion solution.

EXAMPLE 3

Recording Techniques

Cells of the inferior olive were impaled with recording micropipettes 9 under direct vision using Hoffman modulation microscopy (Hoffman, R. J. *Microsc.*, 110: 205-222, 1977; incorporated by reference) which allowed good visualization of the unstained cells. In order to prevent vapor condensation on the objective lens of the microscope 14, a small suction spigot 8 was placed immediately to the side of its bottom surface (FIG. 1A). Intracellular recordings were obtained with micropipettes, 9, filled with 3M potassium acetate or with 1M tetraethylammonium chloride (TEA) having an average D.C. resistance of 60-80 milliohms. The micropipettes were connected to recording amplifier 12. Direct stimulation of the inferior olive cells was implemented with a high-input impedance ($10^{12}$ ohms) bridge amplifier. Capacity compensation allowed a frequency response of 10-15 kHz, depending on the microelectrode properties.

EXAMPLE 4

Blockage of Low-Threshold Calcium Conductance With Octanol

FIG. 3A-C (upper traces) shows intracellular recordings from inferior olivary (I.O.) nuclear cells demonstrating the typical calcium-dependent action potential after the sodium-dependent spike was blocked with $10^{-6}M$ tetrodotoxin (Sigma Chemical Co., St. Louis, Mo.). In this and all examples, I.O. cells were isolated as in Example 1 and recordings were made as in Example 3. The upper row in A, B, C (controls conducted in the absence of octanol) shows the LTCC rebound spike as the high spike. The HTCC is not present because the applied current is subthreshold for the HTCC. The records in the lower row in A, B, C show a complete blockage of the calcium-dependent rebound potentials due to the blockage of LTCC by the application of $10^{-6}M$ octanol to the bath. This is also shown in the "action potential" v. "membrane potential" graph D on the right of FIG. 3 which demonstrates the rate of rise of the low-threshold action potential versus membrane polarization in the control records (closed circles). The lower set of data points (squares) indicates the rate of rise of the low-threshold action potential after octanol at $10^{-6}M$ is added to the perfusion medium. The difference between the control and the octanol graph is a measure of the blocking effect of $10^{-6}M$ octanol on LTCC.

EXAMPLE 5

Inhibition of LTCC by Butanol

FIG. 4A depicts the action potential observed in I.O. neurons under conditions where the sodium channel has been blocked by the addition of tetrodotoxin. Incremental increases in injected square current are applied producing action potential responses shown in FIG. 4A. When a sufficient threshold value is reached, the characteristic spikes of the action potential are produced. The first (left-most) spike is the high-threshold calcium spike and the second (or rebound) spike is the low-threshold calcium spike.

FIG. 4B depicts the resultant action potential upon the administration of $10^{-4}M$ butanol and the inhibition of the LTCC or rebound spike. This effect occurs in the absence of any effect on the HTCC.

EXAMPLE 6

Comparison of the LTCC-Blocking Ability and Relative Efficacy of Alcohols

FIG. 5 depicts a series of tracings, A through H, showing the I.O. cell response to an external square current injection following polarization of the membrane, both in the absence (graphs A-D) and in the presence (graphs E-H) of different types and different concentrations of alcohol. The reduction in the rate of rise of the spike (first differential of the voltage, shown in the middle record) demonstrates the blocking effect of the alcohol on LTCC. This Figure illustrates that higher alkyl alcohols are more effective than lower alcohols or, conversely, that higher alkyl alcohols are as effective but at lower concentrations.

The experiments giving rise to the data of FIG. 5 were conducted as described in Examples 1-3 except that a square current was injected and different alcohols were used, as shown in this figure.

In each of the graphs A through H, the upper trace depicts the action potential observed across the membrane. The middle trace shows the rate of change in the action potential through the cell membrane. Finally, the bottom trace shows the magnitude of the injected current.

In graphs A-D, the cell is shown to have responded with the characteristic low-threshold calcium spike (middle record). By contrast, in graphs F through H, both the rate at which the action potential changes and its magnitude are significantly affected (decreased) by the addition of alcohol. Finally, in graph E, the action potential is lacking the characteristic spike appearance and resembles a subthreshold response.

Comparing graphs E through H, it is observed that butanol appears more than twice as effective as propanol, and that pentanol appears more than five times as effective as butanol.

The above results are all the more significant given that the injected current is 0.5 nA in the alcohol-exposed cells but only 0.25 nA in the control cells. This means that pentanol is really over ten times as effective as butanol which is over four times as effective as propanol. The relative effectiveness increases with the molecular weight of the alcohol. Octanol is preferred because its solubility in aqueous media corresponds closely to the most effective concentration for blocking the LTCC.

EXAMPLE 7

Voltage Clamp Study of Octanol-Induced Blockage of LTCC

The results presented in this Example were recorded in I.O. neurons from different parts of the nucleus. These conductances were characterized by an inward current having a very low threshold ($-70$ mV) which could be observed after the sodium conductance had been blocked by the addition of tetrodoxin and the potassium conductance had been blocked by addition of tetraethyl-ammonium and cesium. In these experiments, the ionic current across the membrane was measured after a voltage clamp pulse was applied across the membrane. In order to maintain the voltage constant, a current must be injected into the cell. This current is equal and opposite to the ionic current across the membrane and thus can be used to determine the size and duration of the ionic current directly. The ionic current generates under normal conditions (not voltage-clamped) the low-threshold calcium spike.

Figure 6:
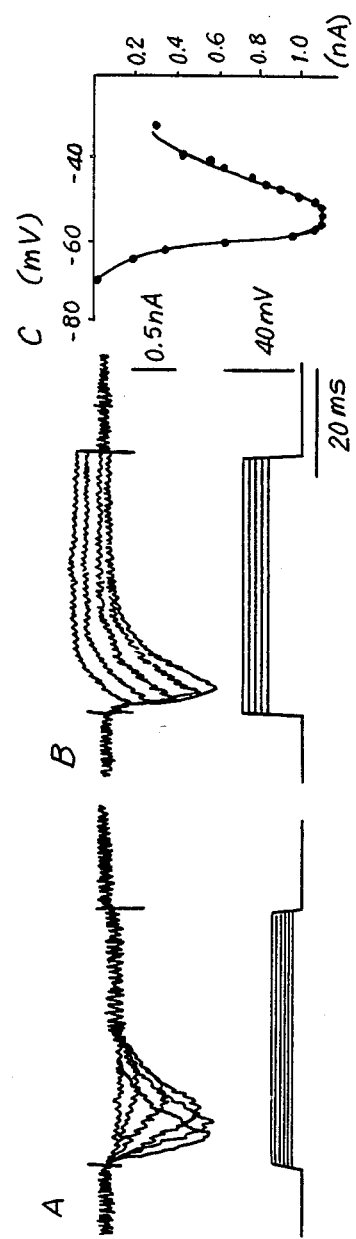
FIG. 6 (A and B) is a series of oscilloscope tracings of the ionic current obtained from I.O. cells at different voltage amplitudes applied using a voltage clamp technique. The graph on the right (C) is a plot of the difference in this ionic current (between the alcohol and the control state) against the applied external voltage.

The results in FIGS. 6A and 6B show the amplitude and time course of the low-threshold calcium ionic currents following depolarization steps of 5 mV from a holding potential of $-80$ mV to a value of $-45$ mV. These records represent the difference in ionic current observed in the control state minus that from the passive ionic current observed after octanol was introduced in the bath. Thus, the records A and B illustrate those ionic currents that were blocked by octanol at $10^{-6}$M (which completely blocked the ionic conductance). An inward current is first observed at $-65$ mV. As the voltage step is incrementally increased in amplitude, the calcium current reaches a peak at a membrane potential step of $-50$ mV, and quickly reduces to null at $-42$ mV, at which potential the calcium channels are inactivated.

FIG. 6C depicts a plot of ionic current against the applied external voltage. The value of this current is the difference between the ionic currents before and after octanol treatment. This difference is maximum at a membrane voltage between about $-45$ and about $-60$ millivolts. This graph characterizes the voltage dependence of the LTCC.

EXAMPLE 8

Blockage of the Rebound Calcium Action Potential

This experiment will be described by reference to FIG. 7, which shows the rebound calcium spike that follows membrane hyperpolarization in the absence of alcohol (A) caused by injection of a square current pulse (C) is blocked by $10^{-6}$M octanol (B).

In this experiment, I.O. cells were treated as described above. The sodium spike was blocked by $10^{-6}$M tetrodoxin.

Figure 7:
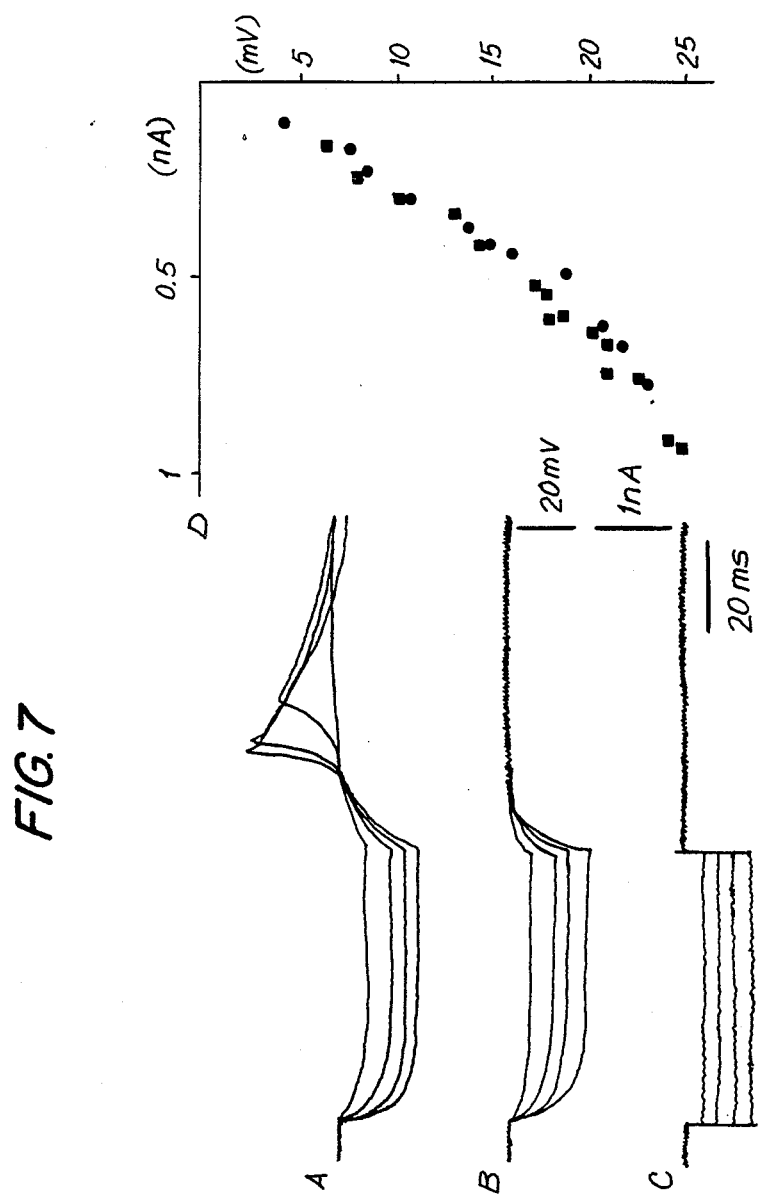
FIG. 7 is a series of oscilloscope tracings of the voltage response across the cell membrane in the absence (A) and presence (B) of octanol (at $10^{-6}$M) pursuant to injection of a hyperpolarizing square current pulse (C). The graph on the right (D) is a plot of the amplitude of the rebound calcium spike against the value of the injected current.

The graph D on the right of FIG. 7 shows the dependence of the rebound calcium spike on the amplitude of the injected hyperpolarizing current.

EXAMPLE 9

Blockage of LTCC In Vivo By Higher Alkyl Alcohols

In order to analyze the effects of LTCC-blocking agents in vivo, octanol was administered to rats. Alcohols were diluted with physiological saline and sonicated to ensure mixing to create a concentration of alcohol around the neurons equivalent to $10^{-6}$M (at most). The alcohol was administered intraperitoneally at a concentration of to 10 mM. Tremor state was induced in the rats by injection of harmaline, an alkaloid derived from Peoamus harmala which has been known to induce tremor in mammals. (Harmaline is available from Sigma Chemical Co., St. Louis, M.) The thus-induced tremor has a periodicity similar to physiological or enhanced physiological tremor.

I.O. cells have been found to be responsible for transmitting the tremor signal to mammalian muscles, since destruction of I.O. cells abolishes tremor in harmaline-treated animals (Llinas, et al., *Science* 190: 1230–1231, 1975). Therefore, study of I.O. cells of mammals in which tremor has been induced with harmaline provides an excellent in vivo model for studying tremor response in mammals.

Tremor can be measured by electromyogram conducted according to Buchthal, F., et al., *Acta Physio. Scand.* 39: 83–104, 1957, incorporated by reference.

The electric activity in the left platysma muscle of 278 to 300 g Sprague-Dawley rats (from Taconic Farms, Germantown, N.Y.) was recorded differentially using two teflon-coated stranded silver wires (2 mm of wire exposed) placed in the belly of the muscle. The electromyogram (emg) was recorded throughout the experiment and the data were analyzed at the following times: (1) before administration of any drugs; (2) after intraperitoneal injection of 15 mg/kg harmaline; and (3) after subsequent intraperitoneal injection of 2 cc of 10 mM 1-octanol (99% octanol sonicated in physiological saline) given to create a concentration of 9.3 micrograms/g of rat body weight or $7 \times 10^{-5}$M in the vicinity of the neuronal cells (if all the alcohol was to be absorbed, and none metabolized). The emg was smoothed and differentiated (to further decrease the background noise) using a Nicolet Explorer Model 4060 digital oscilloscope (from Nicolet Instrument Corp., Madison, Wis.). This instrument was also used to obtain autocorrelograms of 800-ms sections of the emg's. Autocorrelograms were obtained by superimposing 800-ms sections of the emg signals. The emerging patterns (if any) can be used to determine frequency and amplitude characteristics of the emg that may not be readily discernible from the naked emg signal.

Control emg's demonstrated occasional periods of low amplitude oscillations (upper left, FIG. 8). Autocorrelation revealed an 8 Hz periodicity in the emg, but with a low correlation function (upper right, FIG. 8). After harmaline injection, the animals demonstrated periods of generalized tremor. The emg recorded during such a period is illustrated in the middle left-hand trace of FIG. 8; the tremor had a dominant frequency of 7.5 Hz, close to the control value, and showed a high degree of autocorrelation (middle right-hand trace). After injection of of 1-octanol, the tremor stopped and the baseline muscle activity was reduced below control levels (bottom left-hand trace). The dominant frequency was at 10 Hz, and the emg amplitude was so low during this period that it was necessary to amplify the signal in order to obtain an autocorrelogram (bottom, right). Although a 10-Hz periodicity is evident (as shown by the arrows), the 60-Hz frequency due to line voltage (amplifier noise) is the dominant correlation due to the large gain. If the bottom right signal had been amplified only to the extent of the two upper autocorrelograms, it would have appeared as a straight line.

It is evident that, if one wanted to merely decrease the tremor to normal or manageable levels, the amount of alcohol administered would have to be decreased.

What is claimed is:

1. A method for partially or totally blocking low-threshold calcium channels in cell membranes of a mammal in need of such treatment comprising administering to said mammal an aliphatic alcohol selected from the group consisting of $C_2$–$C_{10}$ alkyl alcohols and mixtures thereof in an amount sufficient to generate in the vicinity of said cells a concentration of said alcohol sufficient to partially or totally block low-threshold calcium channels in said cells and insufficient to have a noticeable effect on the high-threshold calcium conductance of said cells.

2. The method of claim 1 wherein said alcohol is octyl alcohol.

3. The method of claim 1 wherein said cells are neuron cells.

4. The method of claim 3 wherein said neuron cells are inferior olivary cells.

5. The method of claim 1 comprising administering to the mammal a composition comprising said low-threshold-calcium conductance blocking effective amount of said alcohol and a physiologically acceptable carrier or diluent.

6. The method of claim 5 comprising administering said alcohol parenterally.

7. The method of claim 5 comprising administering said alcohol orally.

8. The method of claim 5 wherein said composition comprises a diluent selected from the group consisting of Ringer's solution, and isotonic saline solution.

9. A method for inhibiting the manifestation of tremor in a mammal in need of such treatment, the method comprising:
administering to said mammal a tremor-inhibiting effective amount of a low-threshold calcium conductance blocking agent selected from the group consisting of $C_2$–$C_{10}$ alkyl alcohols and mixtures thereof said amount being insufficient to produce a noticeable effect on the high-threshold calcium conductance of cells of said mammal.

10. A method for inhibiting the manifestation of tremor in a mammal in need of such treatment comprising:
administering to said mammal an aliphatic alcohol selected from the group consisting of $C_2$–$C_{10}$ alkyl alcohols and mixtures thereof in an amount effective to partially or totally impede the transmission of a tremor-generating electrical signal from the central nervous system of said mammal to the muscle cells of said mammal that would otherwise exhibit said tremor said amount being insufficient to interfere noticeably with the high-threshold calcium conductance in either the central nervous system cells or the muscle cells of said mammal.

11. A method for inhibiting the manifestation of tremor in a mammal in need of such treatment comprising selectively partially or totally blocking the low threshold calcium channel of the central nervous system cells of said mammal possessing said low-threshold calcium channel by administering to said mammal an amount of an alcohol selected from the group consisting of $C_3$–$C_{10}$ alkyl alcohols and mixtures thereof said amount being sufficient to block said low-threshold calcium channels without producing a noticeable blocking effect on high threshold calcium channels.

12. The method of claim 10 wherein said alcohols are $C_3$–$C_{10}$ alkyl alcohols.

13. The method of claim 12 wherein said central nervous system cells are inferior olivary cells.

14. The method of claim 12 comprising administering to said mammal a composition comprising said low-threshold calcium channel blocking effective amount of an alcohol selected from the group consisting of $C_3$–$C_{10}$ alkyl alcohols and mixtures thereof, and a physiologically acceptable carrier or diluent.

15. The method of claim 13 comprising administering said alcohol orally.

16. The method of claim 13 comprising administering said alcohol parenterally.

17. The method of claim 12 wherein said alcohol is octyl alcohol.

18. The method of claim 14 wherein said alcohol is n-octanol.

19. The method of claim 12 comprising administering to said mammal a composition comprising said effective amount of said alcohol and a physiologically acceptable carrier or diluent.

20. The method of claim 19 wherein said composition is a liquid composition and said diluent is selected from the group consisting of Ringer's solution and isotonic saline.

21. The method of claim 12 comprising administering to said mammal an amount of said alcohol effective to reduce said tremor to normal or manageable levels.

* * * * *